United States Patent [19]

Stokbroekx et al.

[11] Patent Number: 5,112,825
[45] Date of Patent: May 12, 1992

[54] ANTIRHINOVIRAL HETEROAMINE-SUBSTITUTED PYRIDAZINES

[75] Inventors: Raymond A. Stokbroekx, Beerse; Marcel J. M. Van der Aa, Kasterlee, both of Belgium

[73] Assignee: Janssen Pharmaceutica N.V., Beerse, Belgium

[21] Appl. No.: 516,485

[22] Filed: Apr. 30, 1990

Related U.S. Application Data

[63] Continuation-in-part of Ser. No. 351,754, May 15, 1989, abandoned.

[30] Foreign Application Priority Data

May 16, 1989 [GB] United Kingdom ............... 8911158

[51] Int. Cl.⁵ ........................................... C07D 237/06
[52] U.S. Cl. ................................. 514/253; 514/252; 514/212; 514/218; 540/575; 540/598; 544/238; 544/366; 544/368; 544/379; 546/198; 546/212; 548/217; 548/180; 549/64
[58] Field of Search ............ 544/238, 114, 252; 514/253, 252

[56] References Cited

U.S. PATENT DOCUMENTS

| | | | |
|---|---|---|---|
| 2,562,036 | 7/1951 | Hultquist et al. | 548/238 |
| 2,985,657 | 5/1961 | Janssen | 544/238 |
| 3,631,043 | 12/1971 | Regnier et al. | 544/235 |
| 4,101,660 | 7/1978 | Inoue et al. | |
| 4,353,904 | 10/1982 | Thieme et al. | 544/367 |
| 4,451,476 | 5/1984 | Diana | 548/247 |
| 4,556,411 | 12/1985 | Baum | 544/238 |
| 4,590,196 | 5/1986 | Smith et al. | 514/253 |
| 4,818,758 | 4/1989 | Kampe | 514/253 |
| 4,861,791 | 8/1989 | Diana et al. | 514/374 |
| 4,891,375 | 1/1990 | Lowe, III | 514/252 |
| 4,942,241 | 7/1990 | Diana et al. | 548/131 |
| 4,992,433 | 2/1991 | Stokbroekyx et al. | 544/238 |
| 5,001,125 | 3/1991 | Stokbroekx et al. | 544/238 |

FOREIGN PATENT DOCUMENTS

| | | | |
|---|---|---|---|
| 0137242 | 4/1985 | European Pat. Off. | |
| 0156433 | 10/1985 | European Pat. Off. | |
| 0207453 | 1/1987 | European Pat. Off. | |
| 0207454 | 1/1987 | European Pat. Off. | |
| 211157 | 2/1987 | European Pat. Off. | |
| 0211457 | 2/1987 | European Pat. Off. | |
| 0320032 | 6/1989 | European Pat. Off. | 544/238 |
| 2432005 | 2/1975 | Fed. Rep. of Germany | |
| 3819037 | 12/1989 | Fed. Rep. of Germany | |
| 3825170 | 1/1990 | Fed. Rep. of Germany | |
| 2083375 | 9/1988 | Japan | |

OTHER PUBLICATIONS

J. Med. Chem., 15(3) (295-301).

Primary Examiner—Donald G. Daus
Attorney, Agent, or Firm—Charles J. Metz

[57] ABSTRACT

Novel pyridazinamines having antirhinoviral activity, compositions containing these compounds as active ingredient, and a method of inhibiting combating or preventing the growth of viruses in warm-blooded animals suffering from diseases caused by these viruses.

16 Claims, No Drawings

ANTIRHINOVIRAL HETEROAMINE-SUBSTITUTED PYRIDAZINES

CROSS-REFERENCE TO RELATED APPLICATION

This is a continuation-in-part of our copending application Ser. No. 351,754, filed May 15, 1989, now abandoned.

BACKGROUND OF THE INVENTION

In EP-A-0,156,433 are described antivirally active pyridazinamines. Further antiviral agents are described in U.S. Pat. No. 4,451,476; in EP-A-0,137,242 and in EP-A-0,207,453.

The compounds of the present invention differ from the cited art compounds by the fact that they contain a pyridazinamine moiety which is substituted in a previously undisclosed manner and particularly by their favourable antirhinoviral properties.

DESCRIPTION OF THE INVENTION

The present invention is concerned with novel pyridazinamines of formula

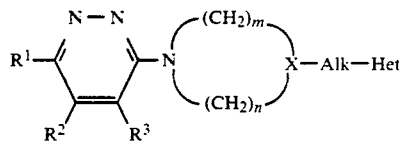

the addition salts thereof and the stereochemically isomeric forms thereof, wherein Het is a radical of formula

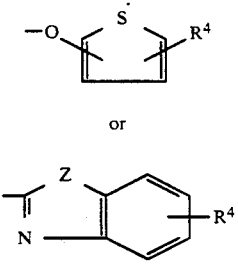

wherein

Z is O, S, SO or $SO_2$; and $R^4$ is cyano or $COOR^5$ wherein $R^5$ represents hydrogen, $C_{1-4}$alkyl, aryl-$C_{1-4}$alkyl, $C_{3-6}$cycloalkyl$C_{1-4}$alkyl, $C_{3-5}$alkenyl, $C_{3-5}$alkynyl or $C_{1-4}$alkyloxy-$C_{1-4}$alkyl, or $R^4$ is a radical of formula

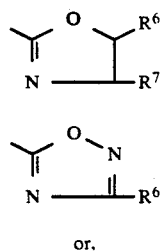

or,

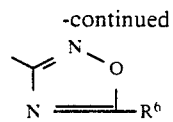

wherein $R^6$ and $R^7$ each independently represent hydrogen, $C_{1-4}$alkyl, aryl or aryl$C_{1-4}$alkyl;

$R^1$ is hydrogen, $C_{1-4}$alkyl, halo, hydroxy, trifluoromethyl, cyano, $C_{1-4}$alkyloxy, $C_{1-4}$alkylthio, $C_{1-4}$alkylsulfinyl, $C_{1-4}$alkylsulfonyl, $C_{1-4}$alkyloxycarbonyl, $C_{1-4}$alkylcarbonyl or aryl;

$R^2$ and $R^3$ each independently are hydrogen or $C_{1-4}$alkyl;

X is CH or N;

m and n each independently are integers of from 1 to 4 inclusive with the sum of m and n being 3, 4 or 5;

Alk is $C_{1-4}$alkanediyl; and each aryl is phenyl, being optionally substituted with 1 or 2 substituents each independently selected from halo, $C_{1-4}$alkyl, trifluoromethyl, $C_{1-4}$alkyloxy or hydroxy.

As used in the foregoing definitions the term "halo" is generic to fluoro, chloro, bromo and iodo; the term "$C_{1-4}$alkyl" defines straight and branch chained saturated hydrocarbon radicals, having from 1 to 4 carbon atoms such as, for example, methyl, ethyl, propyl, 1-methylethyl, butyl, 1,1-dimethylethyl and the like; the term "$C_{3-6}$cycloalkyl" is generic to cyclopropyl, cyclobutyl, cyclopentyl and cyclohexyl; the term "$C_{3-5}$alkenyl" defines straight and branch chained hydrocarbon radicals containing one double bond and having from 3 to 5 carbon atoms such as, for example, 2-propenyl, 3-butenyl, 2-butenyl, 2-pentenyl, 3-pentenyl, 3-methyl-2-butenyl and the like; "$C_{3-5}$alkynyl" defines straight and branch chained hydrocarbon radicals containing one triple bond and having from 3 to 5 carbon atoms such as, propargyl, 2-butynyl, 3-butynyl, 2-pentynyl, 3-pentynyl or 4-pentynyl, and when a $C_{3-5}$alkenyl or $C_{3-5}$alkynyl is substituted on a heteroatom, then the carbon atom of said $C_{3-5}$alkenyl or $C_{3-5}$alkynyl connected to said heteroatom preferably is saturated. "$C_{1-4}$alkanediyl" defines a bivalent straight or branch chained hydrocarbon radical having from 1 to 4 carbon atoms.

The compounds of formula (I) may contain in their structure a keto-enol tautomeric system, and consequently the compounds may be present in their keto form as well as their enol form. These tautomeric forms of the compounds of formula (I) are naturally intended to be embraced within the scope of the invention.

The said addition salts as mentioned hereinabove are meant to comprise the therapeutically active, and in particular, pharmaceutically acceptable non-toxic addition salt forms which the compounds of formula (I) are able to form. The acid addition salts can conveniently be obtained by treating the base form with appropriate acids such as, for example, inorganic acids, such as hydrohalic acid, e.g. hydrochloric, hydrobromic and the like, and sulfuric acid, nitric acid, phosphoric acid and the like; or organic acids such as, for example, acetic, hydroxyacetic, propanoic, 2-hydroxypropanoic, 2-oxopropanoic, ethanedioic, propanedioic, butanedioic, (Z)-2-butenedioic, (E)-2-butenedioic, 2-hydroxybutanedioic, 2,3-dihydroxybutanedioic, 2-hydroxy-1,2,3-propanetricarboxylic, methanesulfonic, ethanesulfonic, benzenesulfonic, 4-methylbenzenesulfonic, cyclohexanesulfamic, 2-hydroxybenzoic, 4-amino-2- hydroxybenzoic and the like acids. Conversely the salt form can be converted by treatment with alkali into the free base form. The compounds of formula (I) containing acidic protons may also be converted into their therapeutically active and in particular, pharmaceutically acceptable non-toxic metal or amine addition salt forms by treatment with appropriate organic and inorganic bases. Appropriate base salt forms comprise, for example, the ammonium salts, the alkali and earth alkaline metal salts, e.g. the lithium, sodium, potassium, magnesium, calcium salts and the like, salts with organic bases, e.g. the benzathine, N-methyl-D-glucamine, hydrabamine salts, and salts with amino acids such as, for example, arginine, lysine and the like. The term acid addition salt also comprises the hydrates and solvent addition forms which the compounds of formula (I) are able to form. Examples of such forms are e.g. hydrates, alcoholates and the like.

From formula (I) it is evident that the compounds of this invention may have an asymmetric carbon atom in their structure. The absolute configuration of this centre may be indicated by the stereochemical descriptors R and S, this R and S notation corresponding to the rules described in Pure Appl. Chem. 1976, 45, 11–30. Unless otherwise mentioned or indicated, the chemical designation of compounds denotes the mixture of all possible stereochemically isomeric forms, said mixtures containing all diastereomers and enantiomers of the basic molecular structure. Stereochemically isomeric forms of the compounds of formula (I) are obviously intended to be embraced within the scope of the invention.

Particular compounds of formula (I) are those compounds within the invention wherein $R^1$ is hydrogen, $C_{1-4}$alkyl, halo, hydroxy or $C_{1-4}$alkyloxy; and/or $R^2$ and $R^3$ are both hydrogen; and/or m and n are both 2.

Other particular compounds are those compounds within the invention wherein $R^4$ is a radical of formula —COOR$^5$ wherein $R^5$ represents $C_{1-4}$alkyl, $C_{3-5}$alkenyl, $C_{3-5}$alkynyl or $C_{1-4}$alkyloxy$C_{1-4}$alkyl or $R^4$ is a heterocycle of formula (b-2) or (b-3) wherein $R^6$ represents hydrogen or $C_{1-4}$alkyl.

Among the above subgroups those compounds of formula (I) are preferred wherein Het is a radical of formula (a-1) or a radical of formula (a-2) wherein Z is O or S; and/or $R^1$ is $C_{1-4}$alkyl or halo; and/or $R^4$ is $C_{1-4}$alkyloxycarbonyl or a 1,2,4-oxadiazol-5-yl of formula (b-2) wherein $R^6$ represents $C_{1-4}$alkyl.

More preferred compounds of formula (I) wherein Het is a radical of formula (a-1) are those compounds within the invention wherein $R^1$ represents methyl, chloro, bromo or iodo; $R^2$ and $R^3$ are both hydrogen; m and n are both 2; and $R^4$ is methoxycarbonyl, ethoxycarbonyl or 3-ethyl-1,2,4-oxadiazo-5-yl.

More preferred compounds of formula (I) wherein Het is a radical of formula (a-2) are those compounds within the invention wherein Z is O or S; $R^1$ represents methyl, chloro, bromo or iodo; $R^2$ and $R^3$ are both hydrogen; m and n are both 2; and $R^4$ is methoxycarbonyl, ethoxycarbonyl or 3-ethyl-1,2,4-oxadiazol-5-yl.

The most preferred compounds within the invention are selected from ethyl 2-[[1-(6-chloro-3-pyridazinyl)-4-piperidinyl]methyl]-6-benzothiazolecarboxylate, ethyl 5-[2-[1-(6-methyl-3-pyridazinyl)-4-piperidinyl]ethoxy]-2-thiophenecarboxylate, ethyl 2-[2-[1-(6-chloro-3-pyridazinyl)-4-piperidinyl]ethyl]-5-benzoxazolecarboxylate, the stereochemically isomeric forms and the pharmaceutically acceptable acid addition salts thereof.

The compounds of formula (I) can generally be prepared by reacting an amine of formula (II) with a pyridazinamine of formula (III) following art-known N-alkylation procedures.

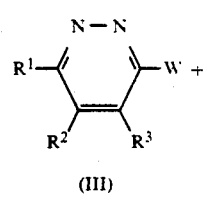

(III)

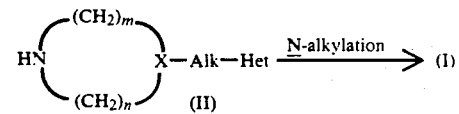

In the foregoing and following reaction schemes W represents an appropriate reactive leaving group such as, for example, halo, e.g. fluoro, chloro, bromo, iodo, or in some instances W may also be a sulfonyloxy group, e.g. 4-methylbenzenesulfonyloxy, benzenesulfonyloxy, 2-naphthalenesulfonyloxy, methanesulfonyloxy, trifluoromethanesulfonyloxy and the like reactive leaving groups.

The N-alkylation reaction can conveniently be carried out by mixing the reactants, optionally in a reaction-inert solvent such as, for example, water; an aromatic solvent, e.g. benzene, methylbenzene, dimethylbenzene, chlorobenzene, methoxybenzene and the like; a $C_{1-6}$alkanol, e.g. methanol, ethanol, 1-butanol and the like; a ketone, e.g. 2-propanone, 2-butanone, 4-methyl-2-pentanone and the like; an ester; e.g. ethyl acetate, γ-butyrolactone and the like; an ether, e.g. 1,1'-oxybisethane, tetrahydrofuran, 1,4-dioxane and the like; a dipolar aprotic solvent, e.g. N,N-dimethylformamide, N,N-dimethylacetamide, dimethylsufoxide, pyridine, 1,3-dimethyl-3,4,5,6-tetrahydro-2(1H)-pyrimidinone, 1,3-dimethyl-2-imidazolidinone, 1,1,3,3-tetramethylurea, 1-methyl-2-pyrrolidinone, nitrobenzene, acetonitrile and the like; or a mixture of such solvents. The addition of an appropriate base such as, for example an alkali metal or an earth alkaline metal carbonate, hydrogen carbonate, hydroxide, oxide, carboxylate, alkoxide, hydride or amide, e.g. sodium carbonate, sodium hydrogen carbonate, potassium carbonate, sodium hydroxide, calcium oxide, sodium acetate, sodium methoxide, sodium hydride, sodium amide and the like, or an organic base such as, for example, a tertiary amine, e.g. N,N-diethylethanamine, N-(1-methylethyl)-2-propanamine, 4-ethylmorpholine, 1,4-diazabicyclo[2.2.2]octane, pyridine and the like, may optionally be used to pick up the acid which is formed during the course of the reaction. In some instances the addition of a iodide salt, preferably an alkali metal iodide, or a crown ether, e.g. 1,4,7,10,13,16-hexaoxacyclooctadecane and the like, may be appropriate. Stirring and somewhat elevated temperature may enhance the rate of the reaction; more in particular the reaction may be conducted at the reflux temperature of the reaction mixture. Additionally, it may be advantageous to conduct said N-alkylation reaction under an inert atmosphere such as, for example, oxygen-free argon or nitrogen gas.

Alternatively, said N-alkylation reaction may be carried out by applying art-known conditions of phase transfer catalysis reactions. Said conditions comprise stirring the reactants, with an appropriate base and optionally under an inert atmosphere as defined hereinabove, in the presence of a suitable phase transfer catalyst such as, for example, a trialkylphenylmethylammonium, tetraalkylammonium, tetraalkylphosphonium, tetraarylphosphonium halide, hydroxide, hydrogen sulfate and the like catalysts. Somewhat elevated temperatures may be appropriate to enhance the rate of the reaction.

In this and the following preparations, the reaction products may be isolated from the reaction mixture and, if necessary, further purified according to the methodologies generally known in the art such as, for example, extraction, distillation, crystallization, trituration and chromatography.

The compounds of formula (I) wherein Het is a radical of formula (a-1), said compounds being represented by (I-a-1), can also be prepared by alkylating a hydroxythiophene of formula (V) with a pyridazinamine derivative of formula (IV).

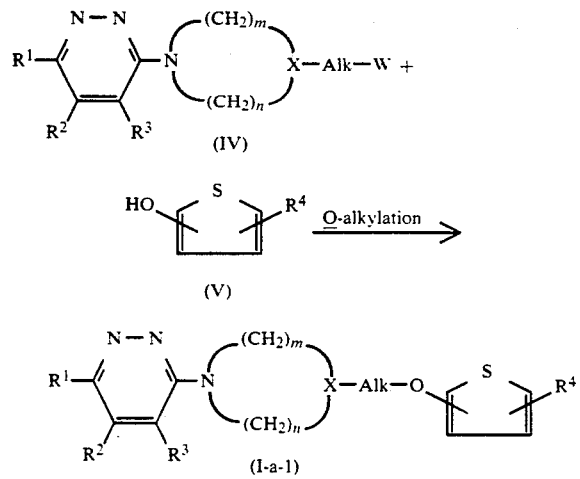

Said O-alkylation reaction can conveniently be carried out by mixing the reactants, optionally in a reaction-inert solvent such as, for example, water; an aromatic solvent, e.g. benzene, methylbenzene, dimethylbenzene and the like; a $C_{1-6}$alkanol, e.g. methanol, ethanol and the like; a ketone, e.g. 2-propanone, 4-methyl-2-pentanone and the like; an ester, e.g. ethyl acetate, γ-butyrolactone and the like; an ether, e.g. 1,1'-oxybisethane, tetrahydrofuran, 1,4-dioxane and the like; a dipolar aprotic solvent, e.g. N,N-dimethylformamide, N,N-dimethylacetamide, dimethylsulfoxide and the like; or a mixture of such solvents. The addition of an appropriate base such as, for example, an alkali metal or an earth alkaline metal carbonate, hydrogen carbonate, hydroxide, oxide, carboxylate, alkoxide, hydride or amide, e.g. sodium carbonate, sodium hydrogen carbonate, potassium carbonate, sodium hydroxide, calcium oxide, sodium acetate, sodium methoxide, sodium hydride, sodium amide and the like, or an organic base such as, for example, a tertiary amine, e.g. N,N-diethylethanamine, N-(1-methylethyl)-2-propanamine and the like, may optionally be used to pick up the acid which is formed during the course of the reaction. Further, it may be advantageous to convert the intermediate of formula (V) first into a suitable salt form thereof such as, for example, an alkali or earth alkaline metal salt, by reacting (V) with an appropriate base as defined hereinabove and subsequently using said salt form in the reaction with the alkylating reagent of formula (IV). Stirring and somewhat elevated temperatures may enhance the rate of the reaction; more in particular the reaction may be conducted at the reflux temperature of the reaction mixture. Additionally, it may be advantageous to conduct said alkylation reaction under an inert atmosphere such as, for example, oxygen-free argon or nitrogen gas.

Alternatively, said O-alkylation reaction may be carried out by applying art-known conditions of phase transfer catalysis reaction as described hereinbefore.

The compounds of formula (I-a-1) can alternatively be prepared by reacting a hydroxythiophene of formula (V) with an alcohol of formula (VI) in the presence of a mixture of diethyl azodicarboxylate and triphenylphosphine.

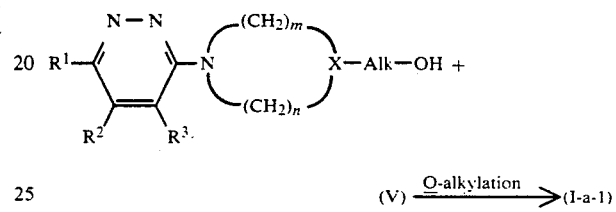

$$(V) \xrightarrow{\text{O-alkylation}} (I\text{-}a\text{-}1)$$

The reaction of (VI) with (V) can conveniently be conducted in an anhydrous reaction-inert solvent preferably under mild neutral conditions at room temperature or below. A suitable reaction-inert solvent is, for example, an aliphatic hydrocarbon, e.g. hexane and the like, an ether, e.g. 1,1'-oxybisethane, 2,2'-oxybispropane, tetrahydrofuran, 1,4-dioxane and the like, a dipolar solvent, e.g. hexamethylphosphoric triamide, N,N-dimethylformamide and the like, or a mixture of such solvents.

The compounds of formula (I-a-1) may also be prepared by reacting an alcohol of formula (VI) with an appropriate reagent of formula (VII) according to the hereinbefore described O-alkylation procedures for the preparation of (I-a-1) from (IV) and (V).

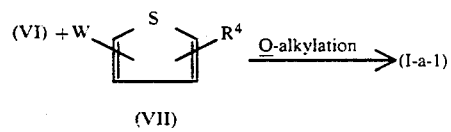

Compounds of formula (I), wherein Het is a radical of formula (a-2), said compounds being represented by (I-a-2), can be prepared by condensing an imidate of formula (VIII) or an acid addition salt form thereof with an amine of formula (IX) in an organic solvent such as, for example, an alcohol, e.g., ethanol, 2-propanol and the like; a halogenated hydrocarbon, e.g. dichloromethane, trichloromethane and the like; an ether, e.g. 1,1'-oxybisethane, tetrahydrofuran, 1,4-dioxane and the like; or mixtures of such solvents.

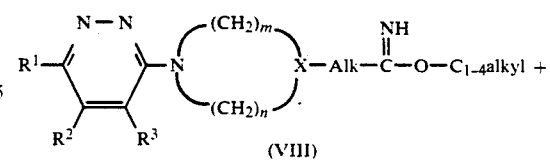

-continued

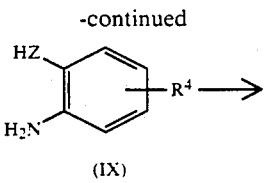

(IX)

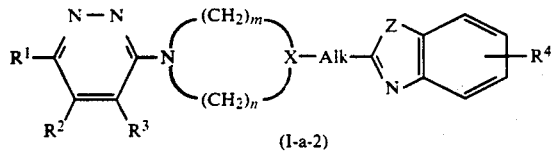

(I-a-2)

Alternatively, the compounds of formula (I-a-2) can be obtained by reacting an acyl halide of formula (X) with an amine of formula (IX) in an organic solvent such as, for example, a halogenated hydrocarbon, e.g. dichloromethane, trichloromethane and the like.

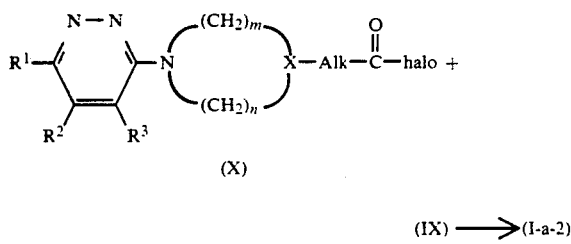

(X)

(IX) $\longrightarrow$ (I-a-2)

The compounds of formula (I-a-2) can also be prepared by condensing an intermediate of formula (XI) with an amine of formula (IX) in a suitable reaction-inert solvent like an alcohol, e.g. ethanol, 2-propanol and the like.

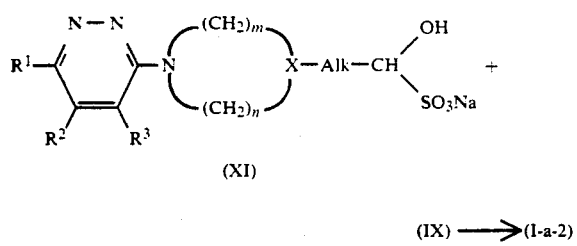

(XI)

(IX) $\longrightarrow$ (I-a-2)

The compounds of formula (I) wherein X is N, said compounds being represented by (I-c), can also be prepared by N-alkylating a pyridazinamine of formula (XII) with a reagent of formula (XIII) following similar procedures as described hereinbefore for the preparation of (I) starting from (II) and (III).

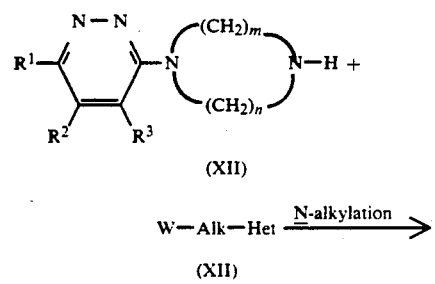

(XII)

W—Alk—Het $\xrightarrow{\text{N-alkylation}}$ (XII)

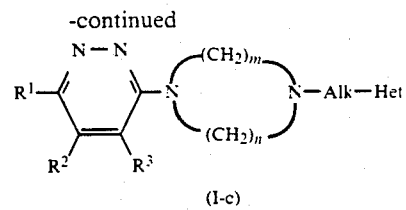

(I-c)

The compounds of formula (I-c) can also be prepared by reductively N-alkylating a pyridazinamine of formula (XII) with a ketone or aldehyde of formula (XIV) following art-known reductive N-alkylation procedures.

(XIV)

In formula (XIV) O=Alk'— represents a radical of formula H—Alk— wherein two geminal hydrogen atoms are replaced by oxygen.

Said reductive N-alkylation reaction may conveniently be carried out by reducing a mixture of the reactants in a suitable reaction-inert solvent. In particular, the reaction mixture may be stirred and/or heated in order to enhance the reaction rate. Suitable solvents are, for example, water; $C_{1-6}$alkanols, e.g. methanol, ethanol, 2-propanol and the like; esters, e.g. ethyl acetate, γ-butyrolactone and the like; ethers, e.g. 1,4-dioxane, tetrahydrofuran, 1,1'-oxybisethane, 2-methoxyethanol and the like; halogenated hydrocarbons, e.g. dichloromethane, trichloromethane and the like; dipolar aprotic solvents, e.g. N,N-dimethylformamide, dimethylsulfoxide and the like; carboxylic acids, e.g. acetic acid, propanoic acid and the like; or a mixture of such solvents.

The term "art-known reductive N-alkylation procedures" means that the reaction is carried out either with sodium cyanoborohydride, sodium borohydride, formic acid or a salt thereof, e.g. ammoniumformate and the like reducing agents, or alternatively under a hydrogen atmosphere, optionally at an increased temperature and/or pressure, in the presence of an appropriate catalyst such as, for example, palladium-on-charcoal, platinum-on-charcoal and the like. In order to prevent the undesired further hydrogenation of certain functional groups in the reactants and the reaction products, it may be advantageous to add an appropriate catalyst-poison to the reaction mixture, e.g. thiophene, quinoline-sulphur and the like. In some instances it may also be advantageous to add an alkali metal salt to the reaction mixture such as, for example, potassium fluoride, potassium acetate and the like salts.

Additionally the compounds of formula (I-c) may be prepared by cyclizing an intermediate of formula (XV) with an amine of formula (XVI).

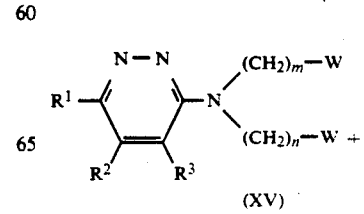

(XV)

$$H_2N-Alk-Het \longrightarrow (I\text{-}c)$$

(XVI)

The reaction is carried out by stirring the reactants in an appropriate organic solvent such as, for example, 2-propanol, cyclohexanol, 2-propanone and the like, optionally in admixture with an appropriate polar solvent preferably at an elevated temperature. Addition to the reaction mixture of an appropriate base, such as, for example, an alkali or an earth alkaline metal carbonate or hydrogen carbonate or an organic base such as, for example, a tertiary amine, e.g. N,N-diethylethanamine may be suited to pick up the acid which is liberated during the course of the reaction. In order to enhance the rate of the reaction a small amount of an appropriate iodide salt, e.g. sodium or potassium iodide may be added.

Compounds of formula (I) wherein X is CH, said compounds being represented by formula (I-d), can be prepared by reacting a ketone (XVII) with an ylide of formula (XIX) or by reacting an aldehyde (XVIII) with an ylide of formula (XX) in a reaction-inert solvent, following art-known Wittig reaction procedures ($R^8$ and $R^9$ are aryl or $C_{1-6}$alkyl) or Horner-Emmons reaction procedures ($R^8$ is alkyloxy and $R^9$ is $O^-$). Appropriate solvents are, for example, hydrocarbons, e.g. hexane, heptane, cyclohexane and the like; ethers, e.g. 1,1'-oxybisethane, tetrahydrofuran, 1,2-dimethoxyethane and the like; dipolar aprotic solvents, e.g. dimethylsulfoxide, hexamethylphosphor triamide, and the like. Then the unsaturated intermediates (XXI) and (XXII) can be reduced following an appropriate reduction procedure, for example, by stirring and, if desired, heating the unsaturated intermediates in a suitable reaction-inert solvent in the presence of hydrogen and an appropriate catalyst such as, for example, palladium-on-charcoal and the like catalysts. Suitable solvents are alkanols, e.g. methanol, ethanol and the like, and carboxylic acids, e.g. acetic acid and the like.

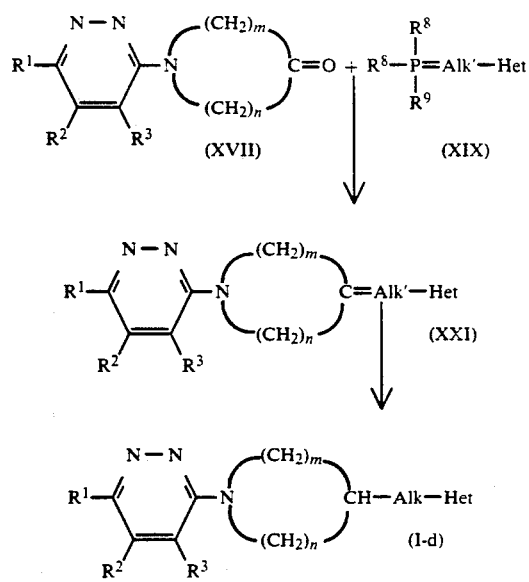

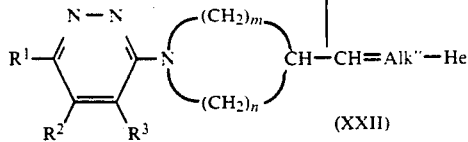

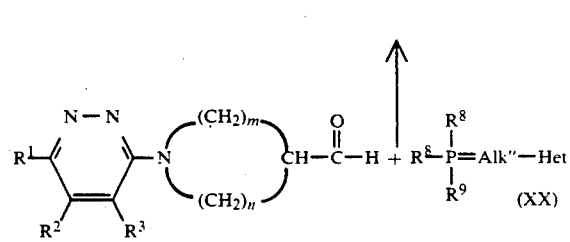

The intermediate ylides of formulae (XIX) and (XX) can be obtained by treating a phosphonium salt or a phosphonate with an appropriate base such as, for example, potassium tert. butoxide, methyllithium, butyllithium, sodium amide, sodium hydride, sodium alkoxide and the like bases under an inert atmosphere and in a reaction-inert solvent such as for example. an ether, e.g. tetrahydrofuran, 1,4-dioxane and the like. In (XIX) $(R^8)_2R^9P=Alk'-$ represents a radical of formula $H-Alk-$ wherein two germinal hydrogen atoms are replaced by $(R^8)_2R^9P=$.

In (XX) Alk'' has the same meaning as Alk' with the proviso that one methylene is lacking.

Alternatively, the compounds of formula (I-d) may be prepared by reacting a ketone (XVII) with an organometallic reagent of formula (XXIII), wherein M represents a metal group such as, for example, lithium, halo magnesium, copper litium and the like, in a reaction-inert solvent such as, for example, an ether, e.g. tetrahydrofuran, 1,1'-oxybisethane, 1,2-dimethoxyethane and the like. The thus prepared alkanol of formula (XXIV) may subsequently be dehydrated with an appropriate acid, e.g. hydrochloric or sulfuric acid, and hydrogenated to a compound of formula (I-d) following the procedure described hereinbefore for reducing intermediate (XXI) to compound (I-d).

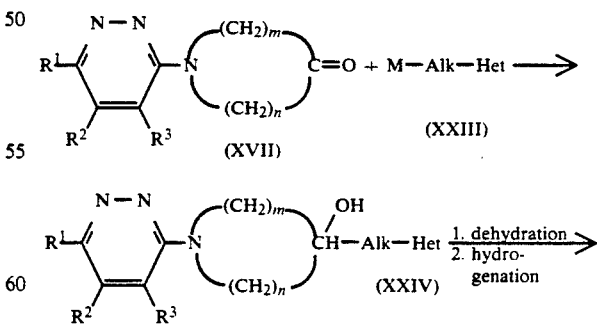

In a similar manner an aldehyde of formula (XVIII) may also be reacted with an organometallic reagent, dehydrated and reduced to yield a compound of formula (I-d).

The compounds of formula (I) can also be converted into each other following art-known functional group transformation procedures.

The compounds of formula (I) wherein $R^4$ is a substituted or unsubstituted 4,5-dihydro-2-oxazolyl radical of formula (b-1), said compounds being represented by formula (I-b-1), can be prepared following procedures described in EP-A-207,454 and EP-A-137,242. For example an appropriate acid, acyl halide or alkyl ester can be condensed with a substituted or unsubstituted hydroxyalkylamine to give a hydroxyalkylamide. The latter may in situ or, if desired, after isolating and purifying it, be cyclized by stirring with thionyl chloride or phosphorous trichloride optionally in the presence of a suitable inert solvent such as, an ether, e.g. tetrahydrofuran, 1,4-dioxane and the like, a halogenated hydrocarbon, e.g. trichloromethane, dichloromethane, an ester, e.g. ethyl acetate, isopropyl acetate and the like solvents.

The compounds of formula (I) wherein $R^4$ is a 1,2,4-oxadiazol-5-yl ring of formula (b-2), said compounds being represented by formula (I-b-2), can be prepared by reacting a compound of formula (I-e), wherein $R^{10}$ is hydrogen or $C_{1-4}$alkyl, with an amidoxime of formula (XXV).

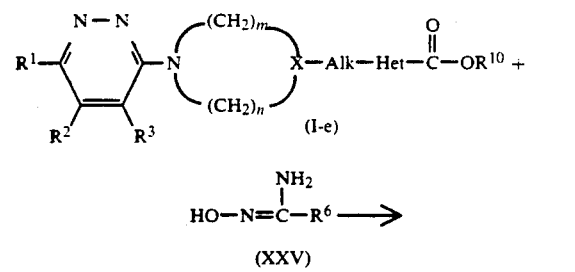

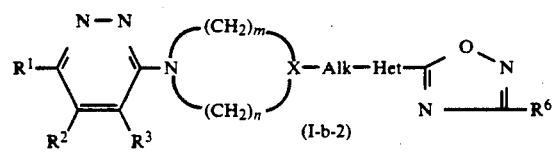

The compounds of formula (I) wherein $R^4$ is a 1,2,4-oxadiazol-3-yl ring of formula (b-3), said compounds being represented by formula (I-b-3), can be prepared by reacting a compound of formula (I) wherein $R^4$ is cyano, represented by formula (I-f), with hydroxylamine or an acid addition salt thereof and reacting the thus formed amidoxime with a carboxylic acid of formula (XXVI) or a reactive functional derivative thereof such as, for example, a halide, an anhydride or an ortho ester form thereof.

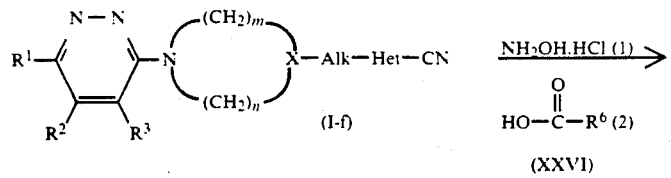

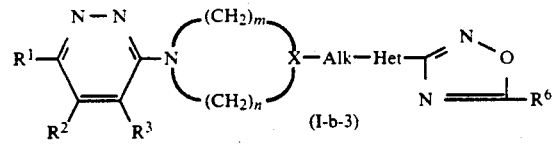

The condensation reactions to prepare compounds (I-b-2) and (I-b-3) can be carried out by stirring and if desired heating the starting materials, neat or in a suitable reaction-inert solvent and optionally in the presence of an appropriate base such as, for example, an alkoxide, hydride or amide, e.g. sodium methoxide, sodium ethoxide, sodium hydride, sodium amide and the like. Suitable solvents for said condensation reactions are for example, ethers, e.g. 1,1'-oxybisethane, tetrahydrofuran, 1,4-dioxane, 1,2-dimethoxyethane and the like; alkanols, e.g. methanol, ethanol, propanol, butanol and the like; or mixtures of such solvents. The water, acid or hydrohalic acid which is liberated during the condensation may be removed from the reaction mixture by azeotropical destillation, complexation, salt formation and the like methods.

The compounds wherein $R^4$ is cyano may be hydrolysed thus yielding compounds of formula (I) wherein the radical $R^4$ is a carboxyl group. Said hydrolysis reaction is preferably conducted in an aqueous acidic medium, e.g. in aqueous sulfuric, hydrochloric or phosphoric acid solution, at room temperature or at a slightly increased temperature. It may be advantageous to add a second acid to the reaction mixture, e.g. acetic acid.

The compounds of formula (I) wherein the radical $R^4$ is a carboxyl group may be converted into the corresponding acyl halides by treatment with a suitable halogenating agent such as, for example, thionyl chloride, pentachlorophosphorane and sulfuryl chloride. Said acyl halides and said acids can further be derivatized to the corresponding esters by reacting said acids or acyl halides with a suitable alkanol following art-known esterification reaction procedures. Said reactions are most conveniently conducted in an appropriate solvent such as, for example, tetrahydrofuran, dichloromethane, trichloromethane, acetonitrile and the like solvents.

The compounds of formula (I) wherein the radical $R^4$ is an ester group may be converted into the corresponding carboxylic acid following art-known saponification procedures, e.g. by treating the starting compound with an aqueous alkaline or an aqueous acidic solution.

The compounds of formula (I) wherein $R^1$ is halo may be converted into compounds of formula (I) wherein $R^1$ is hydrogen following art-known hydrogenolysis procedures, i.e. by stirring and, if desired, heating the starting compounds in a suitable reaction-inert solvent in the presence of hydrogen and an appropriate catalyst such as, for example, palladium-on-charcoal and the like catalysts. Said halo atoms may also be replaced by a $C_{1-4}$alkyloxy or $C_{1-4}$alkylthio substituent by reacting the starting compound with an appropriate alcohol or thioalcohol or, preferably an alkali metal or earth alkaline metal salt of said alcohol or thioalcohol, optionally in the presence of an appropriate catalyst such as, for example, a copper salt. Or, said halo atoms may be replaced by a hydroxy substituent by treatment with an alkanoic acid e.g. acetic acid and subsequent hydrolysis by an aqueous hydrohalic solution. In addition, said halo compounds may also be converted into the corresponding mercapto containing compounds by reacting the former with hydrogen sulfide, sodium hydrogen sulfide, sodium sulfide or a reagent capable of generating hydrogen sulfide, e.g. thiourea in the presence of a base.

The compounds of formula (I) wherein $R^1$ is hydroxy may be converted into compounds of formula (I) wherein $R^1$ is halo by treatment with an halogenating agent such as, for example, thionyl chloride, pentachlorophosphorane, sulfuryl chloride and the like. Or, said hydroxy substituent may be converted into a $C_{1-4}$alkyloxy substituent by O-alkylating the starting compound with an appropriate alkyl halogenide in a suitable reaction-inert solvent.

A number of intermediates and starting materials in the foregoing preparations are known compounds which may be prepared according to art-known methodologies of preparing said or similar compounds and some intermediates are new. A number of such preparation methods will be described hereinafter in more detail.

In the next reaction scheme there are mentioned some different ways of preparing intermediates of formula (XXIX), which can be converted in intermediates of formula (II) wherein Het is a radical of formula (a-1), said intermediates being represented by (II-a-1) by removing the protective group $P^1$. The symbol $P^1$ represents a suitable protective group which is readily removable by hydrogenation or hydrolysis. Preferred protective groups may be, for example, hydrogenolyzable groups e.g. phenylmethyl, phenylmethoxycarbonyl and the like, and hydrolyzable groups, e.g. $C_{1-4}$alkylcarbonyl, $C_{1-4}$alkylphenylsulfonyl and the like.

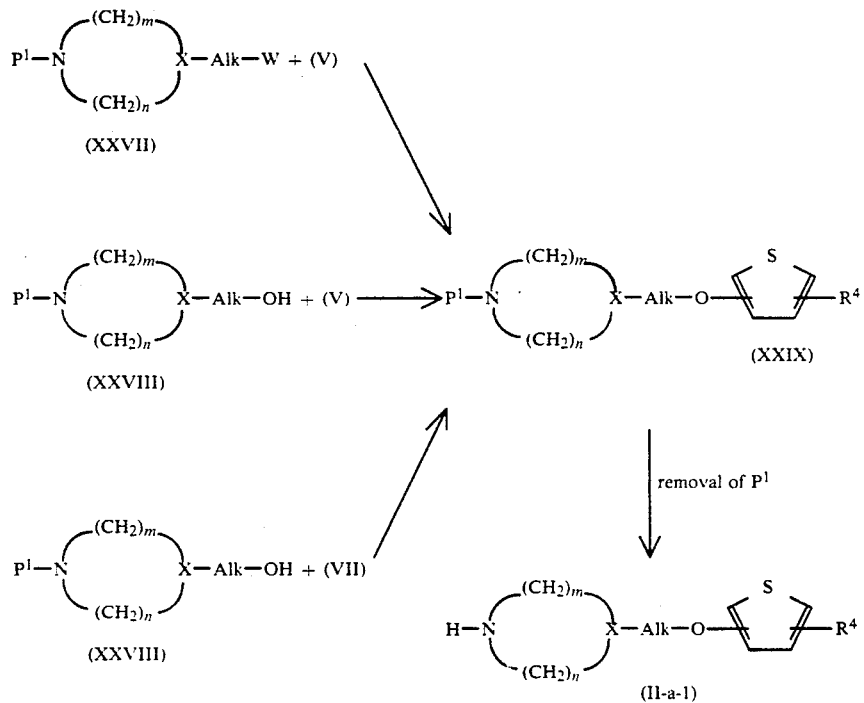

The intermediates of formula (XXIX) can be prepared by O-alkylating a phenol of formula (V) with a reagent of formula (XXVII) or by reacting the phenol (V) with an alcohol of formula (XXVIII) or alternatively by O-alkylating an alcohol of formula (XXVIII) with an appropriate reagent of formula (VII), following the same methods as described hereinbefore for the preparation of (I-a-1).

Intermediates of formula (II) wherein Het is a radical of formula (a-2), said intermediates being represented by formula (II-a-2), can be obtained by removing the protective group $P^1$ in intermediate (XXXIII). This intermediate (XXXIII) can be prepared by condensing an imidate of formula (XXX) or an acid addition salt form thereof with an amine of formula (IX) or by reacting an acyl halide of formula (XXXI) with an ester of formula (IX) or alternatively by condensing an intermediate of formula (XXXII) with an amine of formula (IX), following the same methods as described hereinbefore for the preparation of (I-a-2).

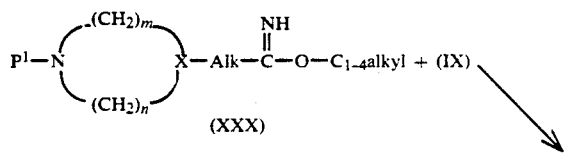

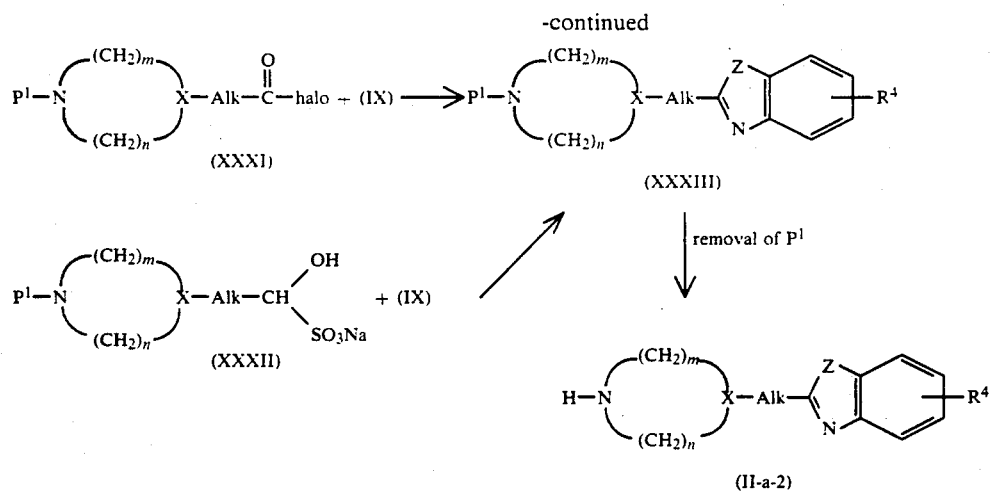

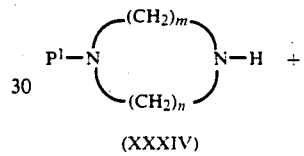

The intermediates of formula (II) wherein X is N, said intermediates being represented by (II-c), can be prepared by N-alkylating an amine of formula (XXXIV) with a reagent of formula (XIII), following N-alkylation procedures as described hereinbefore for the preparation of (I-c), and subsequently removing the protective group $P^1$ in the thus obtained intermediate (XXXV).

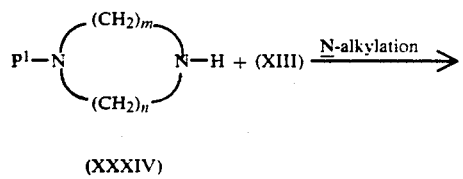

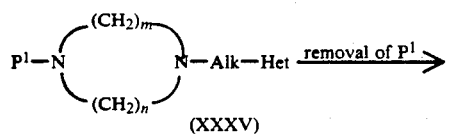

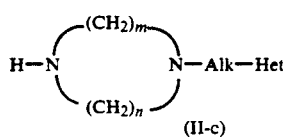

The intermediates of formula (II-c) can alternatively be prepared by reductive N-alkylating an intermediate of formula (XXXIV) with a ketone or aldehyde of formula (XIV) following art-known N-alkylation procedures as described hereinbefore for the synthesis of (I-c) starting from (XII) and XIV) and subsequently removing the protective group $P^1$ in the thus obtained intermediate.

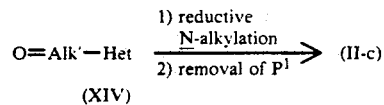

Additionally the intermediates of formula (II-c) may be prepared by cyclizing an intermediate of formula (XXXVI) with an amine of formula (XVI) as described hereinbefore for the preparation of (I-c) from (XV) and (XVI) and subsequently removing the protective group $P^1$ in the thus obtained intermediate (XXXV).

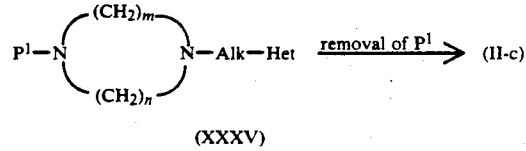

Intermediates of formula (II) wherein X is CH, said intermediates being represented by formula (II-d), can be prepared by reacting a ketone of formula (XXXVII) with an ylide of formula (XIX) or by reacting an aldehyde (XXXVIII) with an ylide of formula (XX). Reduction of the thus obtained intermediates gives intermediates of formula (XXXIX) as described hereinbefore for the preparation of (I-d). Removal of the protective group $P^1$ in (XXXIX) yields the intermediates of formula (II-d).

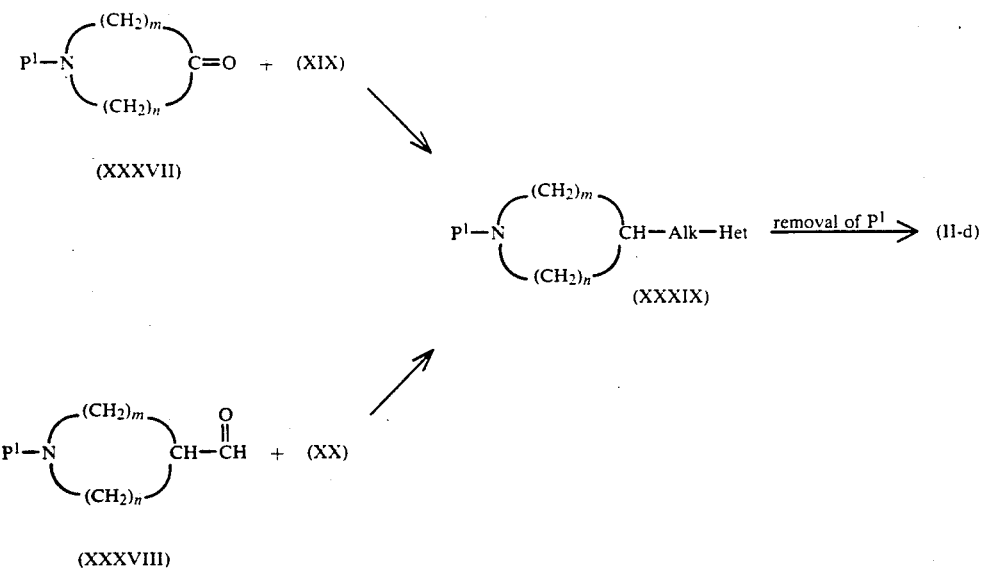

Alternatively, the intermediates of formula (II-d) may be prepared by reacting a ketone of formula (XXXVII) as described hereinbefore for the preparation of (I-b-2) from (I-e) and (XXV).

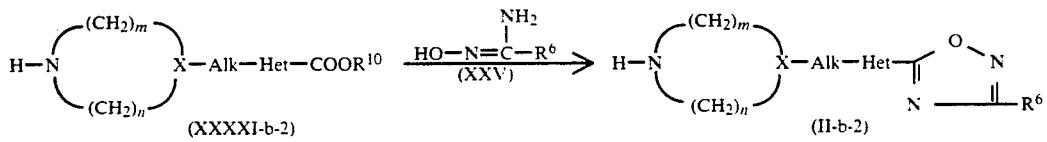

with an organometallic reagent of formula (XXIII). The thus prepared alkanol of formula (XXXX) may subsequently be dehydrated and hydrogenated as described hereinbefore for the preparation of (I-d) from (XVII) and (XXIII). Removal of the protective group P¹ in (XXXX) yields intermediates of formula (II-d). In a similar way an aldehyde of formula (XXXVIII) may also be reacted with an organometallic reagent, dehydrated and reduced to yield a compound of formula (II-d), after removal of the protective group P¹.

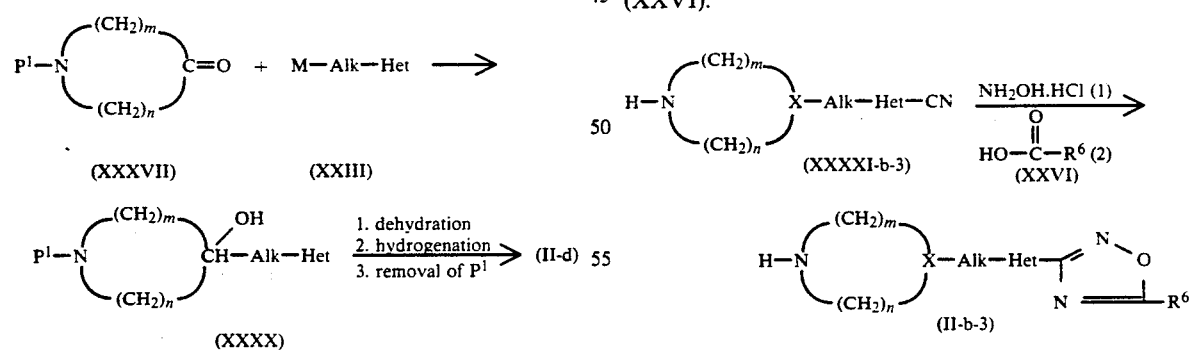

The intermediates of formula (II) wherein R⁴ is a heterocycle of formula (b-1), (b-2) or (b-3), can also be prepared by cyclizing an appropriate piperidinyl or piperazinyl derivative of formula (XXXXI). For example, the intermediates of formula (II) wherein R⁴ is a 1,2,4-oxadiazol-5-yl ring of formula (b-2), said intermediates being represented by formula (II-b-2), can also be prepared by reacting an intermediate of formula (XXXXI-b-2) with an amidoxime of formula (XXV)

The intermediates of formula (II) wherein $R^4$ is a 1,2,4-oxadiazol-3-yl ring of formula (b-3), said intermediates being represented by formula (II-b-3), can be obtained by reacting an intermediate of formula (XXXXI-b-3) with hydroxylamine or an acid addition salt thereof and reacting the thus formed intermediate with a carboxylic acid of formula (XXVI) or a functional derivative thereof, such as, for example, a halide, an anhydride or an ortho ester form thereof. The reaction can be carried out following the same procedure as described for the synthesis of (I-b-3) from (I-f) and (XXVI).

Intermediates of formula (IV) can be prepared by N-alkylating a pyridazine of formula (III) with an amine of formula

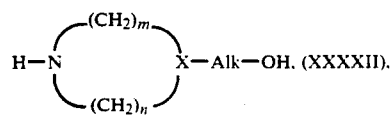

following art-known N-alkylation procedures and subsequently converting the alcohol function of the thus obtained intermediate (VI) into an appropriate leaving group with an appropriate halogenating agent such as, for example, thionyl chloride, sulfuryl chloride, pentachlorophophorane, pentabromophosphorane or an appropriate sulfonyl halide such as, for example, methanesulfonyl chloride or 4-methylbenzenesulfonyl chloride.

The intermediates of formula (XII) can be obtained by reacting intermediates of formula (XXXXIII) with a pyridazine of formula (III) following art-known N-alkylation procedures as described hereinbefore.

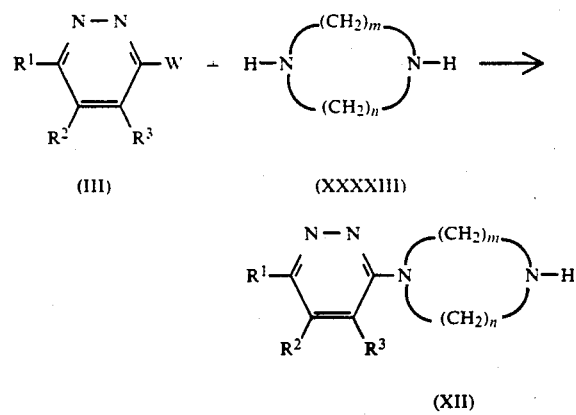

The intermediates of formula (XIII), wherein Het is a radical of formula (a-2), said intermediates being represented by (XIII-a-2) can be prepared by condensing an imidate of formula (XXXXIV) or an acid addition salt form thereof with an amine of formula (IX) or by reacting an acyl halide of formula (XXXXV) with an amine of formula (IX), following the same methods as described hereinbefore for the preparation of (I-a-2).

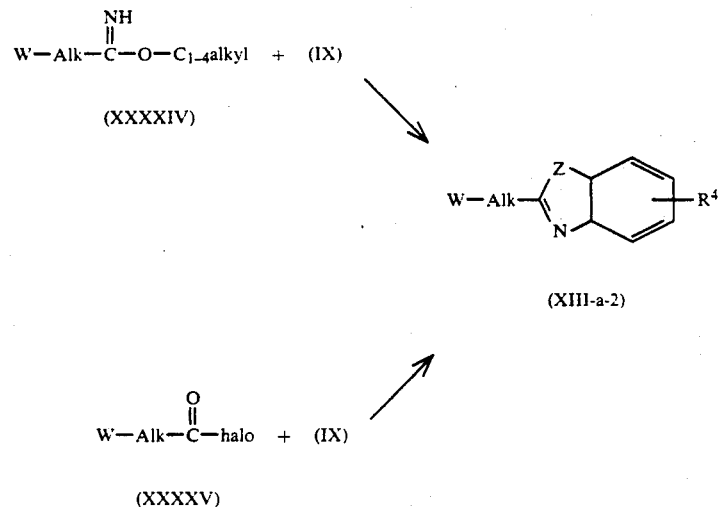

The imidate derivative of formula (XXX) can be prepared by treating the nitrile (XXXXVI) with a lower alkanol preferably methanol or ethanol in the presence of an acid, like hydrochloric acid.

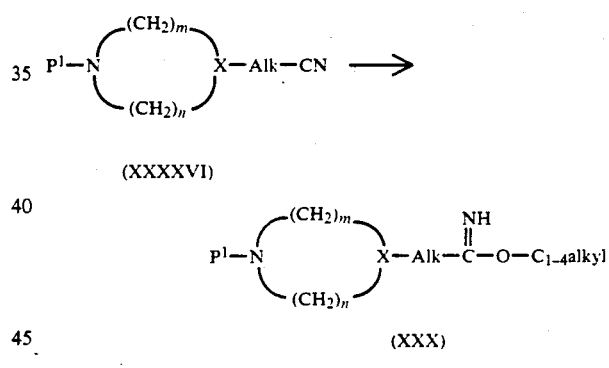

Intermediates of formula (XXXII) can be prepared by reduction of an acyl halide of formula (XXXI) with hydrogen in the presence of an appropriate catalyst like palladium-on-charcoal in a suitable reaction-inert solvent. It also may be advantageous to add an appropriate catalyst-poison to the reaction mixture. The thus obtained aldehyde of formula (XXXXVII) can be treated with sodium hydrogen sulfite to obtain an intermediate of formula (XXXII).

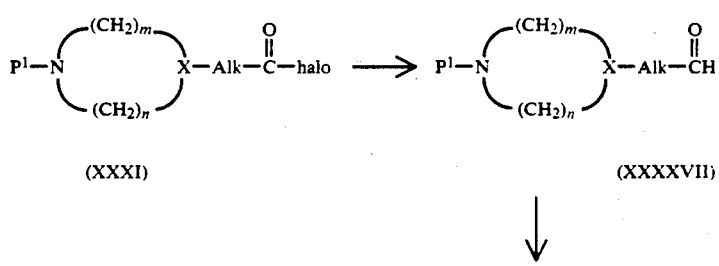

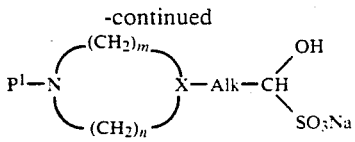

(XXXII)

Starting materials and intermediates used in all of the preceding procedures for which no specific preparation is given herein, may be prepared according similar procedures as described hereinbefore for compounds of formula (I), and/or may be prepared following art-known methodologies described in the literature for the preparation of similar known compounds. For example, intermediates of formula (V) may be prepared following similar procedures described in EP-A-211,157, and the intermediates of formula (XII) may be prepared as described in EP-A-156,433.

The compounds of formula (I) and some of the intermediates in this invention may have an asymmetric carbon atom in their structure. Pure stereochemically isomeric forms of said compounds and said intermediates can be obtained by the application of art-known procedures. For example, diasteroisomers can be separated by physical methods such as selective crystallization or chromatographic techniques, e.g. counter current distribution, liquid chromatography and the like methods. Enantiomers can be obtained from racemic mixtures by first converting said racemic mixtures with suitable resolving agents such as, for example, chiral acids, to mixtures of diastereomeric salts or compounds, then physically separating said mixtures of diastereomeric salts or compounds by, for example, selective crystallization or chromatographic techniques, e.g. liquid chromatography and the like methods; and finally converting said separated diastereomeric salts or compounds into the corresponding enantiomers. Alternatively, enantiomerically pure compounds and intermediates may also be obtained by chromatography of the racemate over a chiral stationary phase and the like techniques. Pure stereochemically isomeric forms of the compounds of formula (I) may also be obtained from the pure stereochemically forms of the appropriate intermediates and starting materials, provided that the intervening reactions occur stereospecifically.

The compounds of formula (I) and the pharmaceutically acceptable addition salts and stereoisomeric forms show antiviral activity and are particularly attractive due to their favourable therapeutic index, resulting from an acceptable low degree of cell toxicity, combined with satisfactory antiviral activity. The antiviral properties of the compounds of formula (I) can be demonstrated for example in the "Picornavirus Minimal Inhibitory Concentration (MIC)"-test, illustrating the useful antiviral activity of the compounds of the present invention.

The compounds of the present invention are therefore useful agents for inhibiting the growth and/or replication of viruses. The compounds of formula (I), the pharmaceutically acceptable addition salts and stereochemically isomeric forms thereof are active against a broad spectrum of picornaviruses, including enteroviruses e.g. Coxsackieviruses, Echoviruses, Enteroviruses, e.g. Enterovirus 70 and especially numerous strains of rhinoviruses, e.g. Human Rhinovirus serotypes HRV-2,-3,-4,-5,-6,-9,-14,-15,-29,-39,-42,-45,-51,-59,-63,-70,-72,-85, -86 and the like.

In view of their potent, local as well as systemic, antiviral activity the compounds of this invention constitute useful tools for inhibiting, combating or preventing the growth of viruses. More particularly there is provided a method of treating viral diseases in warm-blooded animals suffering from said viral diseases, especially respiratory diseases e.g. common cold, pneumonia, bronchiolitis, herpangina and the like, CNS-diseases e.g. paralysis, aseptic meningitis, encephalitis and the like, cardiac disease e.g. pericarditis, myocarditis and the like, hepatic diseases e.g. hepatitis and the like, gastrointestinal diseases e.g. diarrhea and the like, ophtalmic diseases e.g. acute hemorrhagic conjunctivitis and the like, dermatological diseases e.g. exanthem, rash, hand-foot-and-mouth disease, and the like diseases. Said method comprises the systemic or topical administration to warm-blooded animals of an antivirally effective amount of a compound of formula (I), a pharmaceutically acceptable addition salt or a stereoisomeric form thereof. Some compounds of the invention are especially useful to treat respiratory diseases, like common cold due to their prolonged in vivo activity in the buccal and nasal cavity.

The subject compounds may be formulated into various pharmaceutical forms for systemic or topical administration purposes. To prepare the pharmaceutical compositions of this invention, an effective amount of the particular compound, optionally in addition salt form, as the active ingredient is combined in intimate admixture with a pharmaceutically acceptable carrier, which carrier may take a wide variety of forms depending on the form of preparation desired for administration. These pharmaceutical compositions are desired in unitary dosage form suitable, particularly, for administration orally, rectally, percutaneously, intranasally, by parenteral injection or for ophtalimic administration. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions; or solid carriers such as starches, sugars, kaolin, lubricants, binders, disintegrating agents and the like in the case of powders, pills, capsules, and tablets. Because of their ease in administration, tablets and capsules represent the most advantageous oral dosage unit form, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. Also includes are solid form preparations which are intended to be converted, shortly before use, to liquid form preparations. In the compositions suitable for percutaneous administration, the carrier optionally comprises a penetration enhancing agent and/or a suitable wetting agent, optionally combined with suitable additives of any nature in minor proportions, which additives do not introduce a significant deleterious effect on the skin. Said additives may facilitate the administration to the skin and/or may be helpful for preparing the desired compositions. These compositions can take the form of creams, lotions, aerosols and/or emulsions and can be included in a transdermal patch of the matrix or reservoir type as are conventional in the art for this purpose.

In the compositions suitable for topical administration the active ingredient will preferably be a semisolid such as a thickened composition such as salves, creams, gellies, ointments and the like which can be applied by a swab. Pharmaceutical composition suitable for topical administration may also be in form of drops, lotions or an aerosol. Suitable aerosol preparations may include solutions and solids in powder form, which may be in combination with a pharmaceutically acceptable carrier, such as an inert compressed gas. Addition salts of (I) due to their increased water solubility over the corresponding base form, are obviously more suitable in the preparation of aqueous compositions.

In a further aspect of the invention there are provided particular pharmaceutical compositions which comprise a compound of formula (I), a pharmaceutically acceptable addition salt or a stereochemically isomeric form thereof and a cyclodextrin or a derivative thereof. When applied to the site of infection such cyclodextrin based compositions result in a continuous and controlled delivery of sufficiently high concentrations of the antiviral compound of formula (I) to the site of the infection for sustained periods of time.

Such compositions are particularly convenient for treating local viral infections, in particular mucosal infections, e.g. nasal or eye infections.

The cyclodextrin to be used in the aforementioned compositions include the pharmaceutically acceptable unsubstituted and substituted cyclodextrins known in the art, more particularly $\alpha, \beta$ or $\gamma$-cyclodextrins or the pharmaceutically acceptable derivatives thereof.

Substituted cyclodextrins which can be used in the invention include polyethers described in U.S. Pat. No. 3,459,731 which is incorporated by reference for the definition and processes for preparation. In general, unsubstituted cyclodextrins are reacted with an alkylene oxide, preferably under superatmospheric pressure and at an elevated temperature, in the presence of an alkaline catalyst.

Since a hydroxy moiety of the cyclodextrin can be substituted by an alkylene oxide which itself can react with yet another molecule of alkylene oxide, the average molar substitution (MS) is used as a measure of the average number of moles of the substituting agent per glucose unit. The MS can be greater than 3 and theoretically has no limit.

Further substituted cyclodextrins are ethers wherein the hydrogen of one or more cyclodextrin hydroxy groups is replaced by $C_{1-6}$alkyl, hydroxy $C_{1-6}$alkyl, carboxy$C_{1-6}$alkyl or $C_{1-6}$alkyloxycarbonyl$C_{1-6}$alkyl or mixed ethers thereof. In particular such substituted cyclodextrins are ethers wherein the hydrogen of one or more cyclodextrin hydroxy groups is replaced by $C_{1-3}$alkyl, hydroxy$C_{2-4}$alkyl or carboxy$C_{1-2}$alkyl or more in particular by methyl, ethyl, hydroxyethyl, hydroxypropyl, hydroxybutyl, carboxymethyl or carboxyethyl.

In the foregoing definitions the term "$C_{1-6}$-alkyl" is meant to include straight and branched saturated hydrocarbon radicals, having from 1 to 6 carbon atoms, such as, methyl, ethyl, 1-methylethyl, 1,1-dimethylethyl, propyl, 2-methylpropyl, butyl, pentyl, hexyl and the like.

Such ethers can be prepared by reacting the starting cyclodextrin with an appropriate O-alkylating agent or a mixture of such agents in a concentration being selected so that the desired cyclodextrin ether is obtained. The said reaction is preferably conducted in a suitable solvent in the presence of an appropriate base. With such ethers, the degree of substitution (DS) is the average number of substituted hydroxy functions per glucose unit, the DS being thus 3 or less.

In the cyclodextrin derivatives for use in the compositions according to the present invention, the DS preferably is in the range of 0.15 to 3, in particular 0.3 to 2, more in particular 0.3 to 1 and the MS in the range of 0.125 to 10, in particular of 0.3 to 3 and more in particular 0.3 to 1.5.

Other references describing cyclodextrins for use in the compositions according to the present invention, and which provide a guide for the preparation and characteristics of cyclodextrins, for the process of depositing the selected agent within the cavity of the cyclodextrin molecule and for the use of cyclodextrins in pharmaceutical compositions, include the following: "Cyclodextrin Technology" by József Szejtli, Kluwer Academic Publishers (1988) in the chapter Cyclodextrins in Pharmaceuticals; "Cyclodextrin Chemistry" by M. L. Bender et al., Springer-Verlag, Berlin (1978); Advances in Carbohydrate Chemistry", vol. 12 Ed. by M. L. Wolfrom, Academic Press, New York (57) in the chapter The Schardinger Dextrins by Dexter French at p. 189–260; "Cyclodextrins and their Inclusions Complexes" by J. Szejtli, Akademiai Kiado, Budapest, Hungary (1982); I. Tabushi in Acc. Chem. Research, 1982, 15, p. 66–72; W. Sanger, Angewandte Chemie, 92, p. 343–361 (1981); A. P. Croft and R. A. Bartsch in Tetrahedron, 39, p. 1417–1474 (1983); German Offenlegungsschrift DE 3118218; German Offenlegungsschrift DE 3317064; EP-A-94,157; EP-A-149,197; U.S. Pat. No. 4,659,696; and U.S. Pat. No. 4,383,992.

Of particular utility in the invention are the $\beta$-cyclodextrin ethers, e.g. dimethyl-$\beta$-cyclodextrin as described in Drugs of the Future, vol. 9, No. 8, p. 577–578 by M. Nogradi (1984) and polyethers, e.g. hydroxypropyl $\beta$-cyclodextrin and hydroxyethyl $\beta$-cyclodextrin, being examples. Such an alkyl ether may be a methyl ether with a degree of substitution of about 0.125 to 3, e.g. about 0.3 to 2. Such a hydroxypropyl cyclodextrin may for example by formed from the reaction between $\beta$-cyclodextrin an propylene oxide and may have a MS value of about 0.125 to 10, e.g. about 0.3 to 3.

In said particular cyclodextrin based formulation, the molecules of the antiviral compounds of formula (I) are surrounded, at least in part, by the cyclodextrin, i.e. the agent fits into the cyclodextrin cavity.

To prepare said particular cyclodextrin based pharmaceutical compositions of the invention, the selected antiviral compound (or compounds) of formula (I), the pharmaceutically acceptable addition salt of the stereochemically isomeric form thereof is deposited within the cyclodextrin molecule itself, such process being known in the art for other active agents. In the final compositions, the molar ratio of cyclodextrin:antiviral compound is from about 1:1 to about 5:1, in particular, about 1:1 to about 2:1. Thus, in general, the composition will be prepared by dissolving the cyclodextrin in water and adding the antiviral compound to this solution, preferably under vigorous stirring and preferably at a temperature in the range of 10° C. to 50° C., in particular in range of 15° C. to 30° C., and preferably at room temperature.

In the final compositions, the cyclodextrin will comprise about 2.5 to 40% by weight, in particular about 2.5 to 25%, more in particular 5 to 25%, or 5 to 20%, for example about 10%, with the remainder being water, preservative, the active ingredient and any excipients.

In particular, the pharmaceutical compositions may consist only of water, cyclodextrin and the antiviral agents without the need for co-solvents such as ethanol or surfactants.

Application of the cyclodextrin based compositions of the invention may be by aerosol, e.g. with a propellant such as nitrogen, carbon dioxide, a freon, or without a propellant such as a pump spray, drops, or a semisolid such as thickened compositions which can be applied by a swab. In particular applications, semisolid compositions such as salves, creams, gellies, ointments and the like will conveniently be used.

For the liquid preparations of said cyclodextrin based compositions, any of the usual pharmaceutical media may be added, such as, for example, glycols, oils, alcohols and the like, however in concentrations below the level of irritation. In order to stabilize the formulations the pH may be increased or decreased or stabilized by adding appropriate acids, bases or buffer systems, e.g. citrate, phosphate buffers. Further additives may comprise substances to make the formulations isotonic, e.g. sodium chloride, mannitol, glucose and the like. It is further recommendable to add a preservative to the formulations such as, for example, a mercury salt or complex salt, e.g. phenyl mercuriacetate, nitrate, chloride or borate, phenylethyl alcohol, ethanol, propylene glycol and the like. Suitable thickeners for obtaining the above-mentioned thickened compositions comprise polyvinyl alcohols, hydroxypropyl methyl celluloses, hydroxyethyl celluloses, methylcelluloses, polyvinyl pyrrolidone, acrylic acid polymers and the like.

Depending on the type of virus which is to be controlled, said cyclodextrin based compositions can be applied in the vagina, nose, mouth, eyes, lungs or within the cheeks so as to control viruses which have not entered the blood stream of the patient, e.g. viruses which are located in mucous membranes of the body. The cyclodextrin based compositions of the invention are particularly useful on those infection sites where the natural defense mechanisms prevent the delivery of antiviral agents during sustained periods due to an effective elimination of the active compound from the site of infection. Such elimination may be due to clearance by ciliary movement or secretion, or by absorption.

As part of the pharmaceutical composition, one may also include the same or a different active antiviral in a different delivery carrier so as to provide a different profile of activity, e.g. a wide range of time during which the composition shows activity or a supplement to bolster a low level at a particular point in the release schedule of the cyclodextrin.

It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions, drops, teaspoonfuls, tablespoonfuls and the like, and segregated multiples thereof.

Those of skill in treating antiviral diseases in warm-blooded animals could easily determine the effective amount from the test results presented hereinafter. In general it is contemplated that an effective amount would be from 0.001 mg/kg to 50 mg/kg body weight, preferably from 0.01 mg/kg to 10 mg/kg body weight.

The following examples are intended to illustrate and not to limit the scope of the present invention in all its aspects. Unless otherwise stated all parts therein are by weight.

EXPERIMENTAL PART

A. Preparation of the Intermediates

Example 1 a) A mixture of 54 parts of (phenylmethyl)carbonochloridate, 60 parts of ethyl 4-piperidinepropanoate, 31.8 parts of sodium carbonate and 600 parts of trichloromethane was stirred overnight at room temperature. Water was added and the layers were separated. The organic layer was dried, filtered and evaporated. The residue was purified by filtration over silica gel using a mixture of trichloromethane and methanol (99:1 by volume) as eluent. The pure fractions were collected and the eluent was evaporated, yielding 71 parts (74%) of ethyl 1-(phenylmethoxycarbonyl)-4-piperidinepropanoate as a residue (interm. 1).

b) To a stirred and cooled (15° C.) mixture of 11.1 parts of potassium hydroxide and 96 parts of water was added dropwise a solution of 31.8 parts of intermediate 1 in 38 parts of ethanol during 20 minutes. Upon complete addition, stirring was continued overnight at room temperature. The reaction mixture was evaporated at <50° C. The reaction mixture was poured into crushed ice and treated with concentrated hydrochloric acid. The separated aqueous layer was extracted with dichloromethane. The extract was dried, filtered and evaporated, yielding 29 parts (100%) of 1-[(phenylmethoxy)-carbonyl]-4-piperidinepropanoic acid as a residue (interm. 2).

c) To a stirred mixture of 29 parts of intermediate 2 and 520 parts of dichloromethane were added dropwise 14.9 parts of thionyl chloride. Upon complete addition, stirring was continued overnight at room temperature. The reaction mixture was evaporated, yielding 28.3 parts (91.5%) of (phenylmethyl) 4-(3-chloro-3-oxopropyl)-1-piperidinecarboxylate as a residue (interm. 3).

In a similar manner there was also prepared:
(phenylmethyl) 4-(2-chloro-2-oxoethyl-(1-piperidinecarboxylate (interm. 4).

d) To a stirred and cooled (10° C.) solution of 10 parts of ethyl 4-amino-3-mercaptobenzoate in 150 parts of trichloromethane was added dropwise a solution of 15.5 parts of intermediate 3 in 75 parts of trichloromethane. Upon complete addition, the reaction mixture was stirred first overnight at 20° C. and then for 5 hours at reflux temperature. The whole was evaporated, yielding 9 parts (39.8%) of ethyl 2-(2-[1-[(phenylmethoxy)-carbonyl]-4-piperidinyl]ethyl]-6-benzothiazolecarboxylate as a residue (interm. 5).

e) A mixture of 9 parts of intermediate 5 and 100 parts of a hydrochloric acid solution 2N was refluxed overnight. After evaporation, the residue was taken up in 87 parts of methylbenzene and evaporated again (2×). The residue was combined with 80 parts of ethanol and 5 parts of sulfuric acid and the whole was stirred overnight at reflux temperature. The reaction mixture was evaporated, the residue was taken up in crused ice and treated with concentrated ammonium hydroxide. The product was extracted with dichloromethane. The extract was dried, filtered and evaporated. The residue was purified by column chromatography over silica gel using a mixture of dichloromethane, methanol and methanol saturated with ammonia (80:10:10 by volume) as eluent. The eluent of the desired fraction was evaporated, yielding 5 parts (78.5%) of ethyl 2-[2-(4-piperidinyl)ethyl]-6-benzothiazolecarboxylate as an oily residue (interm. 6).

Example 2 a) A mixture of 90 parts of (phenylmethyl) 4-(2- chloro-2-oxoethyl)-1-piperidinecarboxylate, 90 parts of N,N-dimethylacetamide 6 parts of a thiophene solution and 438 parts of 2,2'-oxybispropane was hydrogenated at normal pressure and at room temperature in the presence of 5 parts of palladium-on-charcoal 10%. After the calculated amount of hydrogen was taken up, the catalyst was filtered off and the filtrate was taken up in water. The separated organic layer was dried, filtered and evaporated, yielding 75 parts (95.7%) of (phenylmethyl) 4-(2-oxoethyl)-1-piperidinecarboxylate as a residue (interm. 7).

b) To a stirred mixture of 31.2 parts of sodium hydrogen sulfite and 80 parts of water were added dropwise 47 parts of intermediate 7 at 20° C. Upon complete addition, stirring was continued overnight. The precipitated product was filtered off and 160 parts of ethanol were added. The product was filtered off and dried, yielding 45 parts (68.4%) of (phenylmethyl) 4-[2-(hydroxylsulfonyl)ethyl]-1-piperidinecarboxylate, sodium salt; mp. ±170° C. (interm. 8).

c) A mixture of 5.4 parts of intermediate 8, 3 parts of ethyl 4-amino-3-mercaptobenzoate and 16 parts of ethanol was stirred overnight at reflux temperature. After evaporation, the residue was taken up in water and the product was extracted with dichloromethane. The extract was dried, filtered and evaporated, yielding 7 parts (100%) of ethyl 2-[[1-(phenylmethoxycarbonyl)-4-piperidinyl]methyl]-6-benzothiazolecarboxylate as an oily residue (interm. 9).

d) A mixture of 7 parts of intermediate 9 and 100 parts of a hydrochloric acid solution 2N was refluxed overnight. After evaporation, the residue was taken up in 87 parts of methylbenzene and evaporated again (2x). The residue was combined with 160 parts of ethanol and 3.7 parts of sulfuric acid and stirred for 5 hours at reflux temperature. After evaporation, the residue was taken up in crushed ice and treated with diluted ammonium hydroxide. The product was extracted with 260 parts of dichloromethane. The extract was dried, filtered and evaporated. The residue was purified by column chromatography over silica gel using a mixture of dichloromethane, methanol and methanol saturated with ammonia (80:10:10 by volume) as eluent. The eluent of the desired fraction was evaporated, yielding 4.5 parts (98.5%) of ethyl 2-(4-piperidinylmethyl(-6-benzothiazolecarboxylate as an oily residue (interm. 10).

Example 3 a) To a stirred mixture of 9.1 parts of ethyl 3-amino-4-hydroxybenzoate and 150 parts of trichloromethane was added dropwise a solution of 15.5 parts of intermediate 3 in 75 parts of trichloromethane at 5° C. Upon completion, stirring was continued first overnight at room temperature and then for 5 hours at reflux temperature. After evaporation, the residue was combined with a small amount of 4-methylbenzenesulfonic acid and 135 parts of dimethylbenzene. The reaction mixture was refluxed for 6 hours using a water separator. After cooling, water was added and the layers were separated. The organic layer was dried, filtered and evaporated, yielding 7 parts (32.1%) of ethyl 2-2-(1-[(phenylmethoxy)carbonyl]-4-piperidinyl]ethyl]-5-benzoxazolecarboxylate as a residue (interm. 11).

b) A mixture of 7 parts of intermediate 11 and 200 parts of ethanol was hydrogenated at normal pressure and at 50° C. in the presence of 2 parts of palladium-on-charcoal catalyst 10%. After the calculated amount of hydrogen was taken up, the catalyst was filtered off and the filtrate was evaporated, yielding 4 parts (82.7%) of ethyl 2-[2-(4-piperidinyl)-ethyl]-5-benzoxazolecarboxylate as a residue (interm. 12).

Example 4 a) 2350 Parts of hydrogen chloride were bubbled through 5600 parts of cooled ethanol (ice-bath) at 10° C. Then there were added dropwise, during a 45 minutes-period, 1500 parts of 1-(phenylmethyl)-4-piperidineacetonitrile. Upon completion, the whole was stirred for 20 hours at room temperature. The reaction mixture was evaporated and the residue was stirred in 2400 parts of acetonitrile. The product was filtered off, washed with 560 parts of acetonitrile and dried, yielding 2000 parts (85.7%) of O-ethyl 1-(phenylmethyl)-4-piperidineethanimidate dihydrochloride (interm. 13).

b) A mixture of 40 parts of intermediate 13, 21 parts by ethyl 3-amino-4-hydroxybenzoate and 237 parts of ethanol was stirred overnight at reflux temperature. The reaction mixture was evaporated and 100 parts of ice-water were added to the residue. The whole was basified with NH4OH (conc.) and the product was extracted with dichloromethane. The extract was dried, filtered and evaporated and the residue was purified twice by column chromatography (silica gel; CHCl3/CH3OH 98:2; CHCl3/CH3OH 99:1). The eluent of the desired fraction was evaporated, yielding 10 parts (22.0%) of ethyl 2-[[1-(phenylmethyl-4-piperidinyl]methyl]-5-benzoxazolecarboxylate (interm. 14).

c) A mixture of 10 parts of intermediate 14 and 198 parts of ethanol was hydrogenated at normal pressure and at 50° C. with 2 parts of palladium-on-charcoal catalyst 10%. After the calculated amount of hydrogen was taken up, the catalyst was filtered off and the filtrate was evaporated, yielding 5 parts (66.7%) of ethyl 2-(4-piperidinylmethyl)-5-benzoxazolecarboxylate (interm. 15).

Example 5 a) To a stirred mixture of 175.4 parts of ethyl 4-piperidineacetate, 116.6 parts of sodium carbonate and 2250 parts of trichloromethane were added dropwise 119.4 parts of ethyl chloroformate. After stirring for 4 hours at temperature, the reaction mixture was diluted with 400 parts of water. The organic layer was separated, dried, filtered and evaporated, yielding 277 parts (100%) of ethyl 1-(ethoxycarbonyl)-4-piperidineacetate (interm. 16).

b) A mixture of 168 parts of potassium hydroxide and 1000 parts of water was stirred at 10° C. There were added 249.4 parts of intermediate 16 and 400 parts of ethanol at 20° C. and stirring was continued overnight at room temperature. The solvent was evaporated and the cooled residue was diluted with water and acidified with hydrochloric acid while keeping the temperature below 20° C. The product was extracted with dichloromethane (2×520 parts) and the combined extracts were washed with water, dried, filtered and evaporated. The residue was suspended in hexane (2×) and then solidified upon stirring in 2,2'-oxybispropane. The product was filtered off and dried, yielding 170.7 parts of 1-(ethoxycarbonyl)-4-piperidineacetic acid (interm. 17).

c) To 960 parts of thionyl chloride were added 155.15 parts of intermediate 17 at 10° C. After stirring overnight at room temperature, the reaction mixture was evaporated. The residue was distilled, yielding 157 parts (93.3%) of ethyl 4-(2-chloro-2-oxoethyl)-1-piperidinecarboxylate; bp. 140°-145° C. (interm. 18).

d) A mixture of 157 parts of intermediate 18, 75 parts of 2,6-dimethylpyridine and 1890 parts of tetrahydrofuran was hydrogenated at normal pressure and room temperature with 15 parts of palladium-on-charcoal catalyst 10%. After the calculated amount of hydrogen was taken up, the catalyst was filtered off and the filtrate was evaporated. The residue was dissolved in dichloromethane. This solution was washed with diluted hydrochloric acid (2×) and water, dried, filtered and evaporated. The residue was distilled, yielding 122.7 parts (91.6%) of ethyl 4-(2-oxoethyl)-1-piperidinecarboxylate; bp. 125°-130° C. at 133 Pa (interm. 19).

e) A mixture of 13.9 parts of intermediate 19, 39.5 parts of methanol and 5 parts of potassium acetate was hydrogenated at normal pressure and at room temperature with 3 parts of Raney nickel. After the calculated amount of hydrogen was taken up, the catalyst was filtered off and the filtrate was evaporated. The residue was taken up in water and the product was extracted with methylbenzene. The extract was dried, filtered and evaporated, yielding 8.3 parts (58.9%) of ethyl 4-(2-hydroxyethyl)-1-piperidinecarboxylate (interm. 20).

f) A mixture of 8.3 parts of intermediate 20 and 176 parts of hydrochloric acid 35% was stirred for 1 hour at reflux temperature. The reaction mixture was evaporated, yielding 6.1 parts (89.8%) of 4-piperidineethanol hydrochloride (interm. 21).

g) A mixture of 6.1 parts of 3,6-dichloropyridazine, 6.8 parts of intermediate 21, 21 parts of sodium carbonate and 188 parts of N,N-dimethylformamide was stirred overnight at 60° C. The reaction mixture was evaporated and the residue was partitioned between water and trichloromethane. The organic layer was dried, filtered and evaporated and the residue was purified by column chromatography (silica gel; CHCl₃/CH₃OH 97:3). The eluent of the desired fraction was evaporated, yielding 5.2 parts (52.5%) of 1-(6-chloro-3-pyridazinyl)-4-piperidineethanol (interm. 22).

h) To 5.1 parts of thionyl chloride was added dropwise a solution of 5.2 parts of intermediate 22 in 133 parts of dichloromethane. After stirring overnight at room temperature, the reaction mixture was evaporated. The residue was partitioned between water and trichloromethane. The organic layer was dried, filtered and evaporated, yielding 5.3 parts (94.8%) of 3-chloro-5-[4-(2-chloroethyl-1-piperidinyl]pyridazine (interm. 23).

Example 6

A mixture of 19.3 parts of 3-chloro-6-methylpyridazine, 19.4 parts of 4-piperidinethanol, 16 parts of sodium carbonate and 0.85 parts of N,N-dimethylacetamide was stirred for 5 hours at 150° C. After cooling, the reaction mixture was diluted with water and extracted with dichloromethane (2×). The combined extracts were washed with water, dried, filtered and evaporated. The residue was purified by column chromatography (silica gel;CHCl₃/CH₃OH 98:2). The eluent of the desired fraction was evaporated, yielding 23.6 parts (71.1%) of 1-(6-methyl-3-pyridazinyl)-4-piperidineethanol; p. 99°-100° C. at 8 Pa (interm. 24).

Example 7

A mixture of 9 parts of ethyl 3-amino-4-hydroxybenzoate, 10.2 parts of ethyl 4-chlorobutanimidate hydrochloride and 150 parts of trichloromethane was stirred for 24 hours at 20° C. The separated organic layer was dried, filtered and evaporated. The residue was purified by column chromatography over silica gel using a mixture of trichloromethane and methanol (98:2 by volume) as eluent. The eluent of the desired fraction was evaporated, yielding 10 parts (74.7%) of ethyl 2-(3-chloropropyl)-5-benzoxazolecarboxylate as a residue (interm. 25).

In a similar manner there was also prepared: ethyl 2-(chloromethyl)-5-benzoxazolecarboxylate (interm. 26).

Example 8

To a stirred and cooled (0° C.) solution of 26.6 parts of ethyl 4-amino-3-mercaptobenzoate in 450 parts of trichloromethane were added slowly 16.8 parts of chloroacetyl chloride. Stirring was continued for 2 hours at reflux temperature. After cooling to 20° C., the undissolved part was filtered off and the filtrate was evaporated. The residue was purified by column chromatography over silica gel using trichloromethane as eluent. The pure fractions were collected and the eluent was evaporated, yielding 21 parts (61%) of ethyl 2-chloromethyl)-6-benzothiazolecarboxylate (interm. 27).

Example 9

A mixture of 4.32 parts of 4-hydroxy-2-thiophenecarboxylic acid (described in Chem. Ber. 87, p. 835) and 5.04 parts of sodium hydrogen carbonate was dried azeotropically with 121.5 parts of 2-butanone under a nitrogen atmosphere. The mixture was then refluxed using a water separator, while a solution of 4.62 parts of diethyl sulfate in 40.5 parts of 2-butanone was added dropwise. Refluxing was continued overnight. After cooling, the reaction mixture was filtered and the filtrate was evaporated, yielding 4.6 parts (89.0%) of ethyl 4-hydroxy-2-thiophenecarboxylate (interm. 28).

B. Preparation of the Final Compounds

Example 10

A mixture of 2.24 parts of 3-chloro-6-methylpyridazine, 5 parts of intermediate 15, 1.85 parts of sodium carbonate and 3 drops of N,N-dimethylacetamide was stirred for 8 hours at 140° C. After cooling, water was added and the product was extracted with dichloromethane. The extract was dried, filtered and evaporated and the residue was purified by column chromatography (silica gel; CHCl$_3$/CH$_3$OH 99:1). The eluent of the first fraction was evaporated and the residue was crystallized from a mixture of 2-propanol and 2,2'-oxybispropane, yielding 0.9 parts (13.6%) of ethyl 2-[[1-(6-methyl-3-pyridazinyl)-4-piperidinyl]methyl]-5-benzoxazolecarboxylate. Evaporation of the eluent of the second fraction and subsequent crystallisation from 2,2'-oxybispropane yielded another 0.7 parts (10.6%) of ethyl 2-[[1-(6-methyl-3-pyridazinyl)-4-piperidinyl]methyl]-5-benzoxazolecarboxylate. Total yield: 1.6 parts (24.2%) (comp. 1).

Example 11

A mixture of 2.2 parts of 3,6-dichloropyridazine, 4.5 parts of intermediate 10, 5.3 parts of sodium carbonate and 94 parts of N,N-dimethylformamide was stirred overnight at 65° C. After evaporation, the residue was taken up in water and the product was extracted with dichloromethane. The extract was dried, filtered and evaporated. The residue was crystallized from ethanol, yielding 0.3 parts (4.8%) of ethyl 2-[[1-(6-chloro-3-pyridazinyl)-4-piperidinyl]methyl]-6-benzothiazolecarboxylate; mp. 158.4° C. (compound 2).

In a similar manner there were also prepared:

ethyl 2-[2-[1-(6-chloro-3-pyridazinyl)-4-piperidinyl]ethyl]-6-benzothiazolecarboxylate; mp. 124.4° C. (compound 3); and
ethyl 2-[2-[1-(6-chloro-3-pyridazinyl)-4-piperidinyl]ethyl]-5-benzoxazolecarboxylate; mp. 128.6° C. (compound 4).

Example 12

A mixture of 3.9 parts of intermediate 23, 2.6 parts of intermediate 28, 4.2 parts of potassium carbonate and 188 parts of N,N-dimethylformamide was stirred overnight at 130° C. while nitrogen was bubbled through. After cooling, the reaction mixture was poured into water and the whole was extracted with dichloromethane. The extract was dried, filtered and evaporated. The residue was purified by column chromatography (silica gel; CHCl$_3$/C$_2$H$_5$OH 99.5:0.5). The eluent of the desired fraction was evaporated and the residue was crystallized from 2-propanol, yielding 0.8 parts (13.5%) of ethyl 4-[2-[1-(6-chloro-3-pyridazinyl)-4-piperidinyl]ethoxy]-2-thiophenecarboxylate; mp. 111.7° C. (compound 5).

In a similar manner there was also prepared: ethyl 5-[2-[1-(6-chloro-3-pyridazinyl)-4-piperidinyl]ethoxy]-2-thiophenecarboxylate; mp. 86.8° C. (comp. 6).

Example 13

To a stirred solution of 2.7 parts of intermediate 24, 2.3 parts of ethyl 5-hydroxy-2-thiophenecarboxylate and 31.5 parts of triphenylphosphine in 180 parts of tetrahydrofuran was added dropwise a solution of 2.1 parts of diethyl azocarboxylate in 45 parts of tetrahydrofuran while cooling at ≦10° C. Upon complete addition, the reaction mixture was stirred overnight at room temperature. After evaporation, the residue was taken up in water and the product was extracted with dichloromethane. The extract was dried, filtered and evaporated. The residue was purified by column chromatography over silica gel using a mixture of trichloromethane and ethanol (99:1 by volume) as eluent. The eluent of the desired fraction was evaporated and crystallized from 2-propanol and petroleum ether, yielding 0.43 parts (9.5%) of ethyl 5-[2-[1-(6-methyl-3-pyridazinyl)-4-piperidinyl]ethoxy]-2-thiophenecarboxylate; mp. 114.1° C. (compound 7).

Example 14

A mixture of 4 parts of 3-chloro-6-(1-piperazinyl)-pyridazine, 6 parts of intermediate 26, 5.3 parts of sodium carbonate and 94 parts of N,N-dimethylformamide was stirred overnight at 80° C. After evaporation, the residue was taken up in water. The precipitated product was filtered off, washed with water and dissolved in dichloromethane. The organic layer was dried, filtered and evaporated. The residue was crystallized from 2-propanol, yielding 5 parts (62.2%) of ethyl 2-[[4-(6-chloro-3-pyridazinyl)-1-piperazinyl]methyl]-5-benzoxazolecarboxylate; mp. 139.6° C. (compound 8).

In a similar manner there were also prepared:

ethyl 2-[3-[4-(6-chloro-3-pyridazinyl)-1-piperazinyl]propyl]-5-benzoxazolecarboxylate; mp. 130.1° C. (compound 9); and
ethyl 2-[[4-(6-chloro-3-pyridazinyl)-1-piperazinyl]methyl]-6-benzothiazolecarboxylate; mp. 176.6° C. (compound 10).

C. Biological Examples

The strong antiviral activity of the compounds of formula (I) is clearly evidenced by the data obtained in the following experiment, which data are only given to illustrate the useful antiviral properties of all the compounds of formula (I) and not to limit the invention either with respect to the scope of susceptible viruses nor with respect to the scope of formula (I).

Example 15: Picornavirus Minimal Inhibitory Concentration Test.

The Minimal Inhibitory Concentration of the compounds of the present invention against the Human Rhinovirus strains (HRV) -2,-9,-14,-15,-29,-39,-41,-42,-45,-51, -59,-63,-70,-72,-85,-86 and -89 was determined by a standard cytopathic effect reduction assay as follows. To each of the ninty six (96) wells of a microtiter 96 well tissue culture plate there was added 60 μl of a Ohio Hela cell maintenance medium [Eagle's Basal medium supplemented with 5% Foetal Calf Serum (FCS)]. To two wells there was added 60 μl of an appropriate starting dilution of a compound of formula (I) and two-fold dilutions were made to cover a wide range of compound concentrations. Subsequently there were added 120 μl of an infectious solution of virus in Eagle's Basal Medium with 2% Hepes buffer, 2% FCS and 30 mM MgCl$_2$ to all wells except cell and compound controls. Said infectious virus solution having a TCID$_{50}$-value (Tissue Culture Infectious Dose) of about 100.

The TCID$_{50}$-value is the dose of viruses which initiates a cytopathic effect in 50% of the inoculated cells. 150 μl of the thus obtained virus-compound mixtures were then transferred to microtiter plates with subconfluent Ohio Hela Cells, grown in 100 μl of maintenance medium. Appropriate virus controls, cell controls and compound controls were included in each test. Plates were incubated for 3 to 5 days at 33° C. in 5% CO$_2$ atmosphere. They were checked daily by light microscopy without staining and read when the virus controls showed 100% cytopathic effect (CPE) and the virus back titration confirmed that a $TCID_{50}$-value between 32 and 256 had been used in the test. The $IC_{50}$-value for each virus-compound series was taken as the concentration in ng/ml that protected 50% of the cells from cytopathic effects with respect to the untreated controls. In the standard test procedure, the compounds were tested against a first panel of rhinoviruses consisting of serotypes HRV-2,-29,-39-85,-9,-15,-51,-59,-63,-89 and -41 and the other panel consisting of HRV-42,-45,-14,-70,-72 and -86.

The $IC_{50}$-value for each rhinovirus serotype was determined, and the efficacy of each compound was determined in terms of the $Med_1$-value and $Med_2$-value, which is the medium value of the $IC_{50}$-values of all serotypes from the first and second panel respectively.

The following table gives the testing results with the compounds of the invention.

| Activity of antirhinoviral compounds | | |
|---|---|---|
| Comp. No. | $Med_1$(ng/ml) | $Med_2$(ng/ml) |
| 2 | 31 | 67 |
| 7 | 7 | 185 |
| 4 | 88 | 39 |

We claim:

1. A compound of the formula:

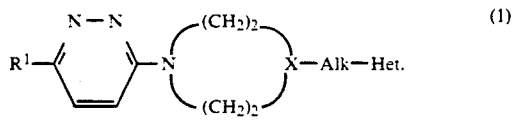

an addition salt thereof or a stereochemically isomeric form thereof, wherein:

Het is a radical of the formula:

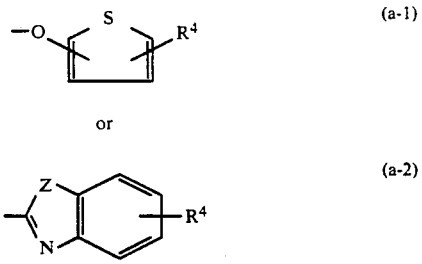

wherein

Z is O, S, SO, or $SO_2$; and $R^4$ is a radical of formula —$COOR^5$ wherein $R^5$ represents $C_{1-4}$alkyl, $C_{3-5}$alkenyl, $C_{3-5}$alkynyl, or $C_{1-4}$alkyloxy$C_{1-4}$alkyl, or $R^4$ represents a radical of the formula:

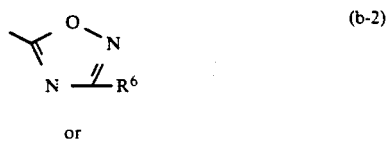

-continued

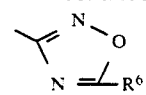

wherein $R^6$ represents hydrogen or $C_{1-4}$alkyl;

$R^1$ is hydrogen, $C_{1-4}$alkyl, halo, hydroxy, or $C_{1-4}$alkyloxy; and

X is CH or N.

2. A compound according to claim 1 wherein Het is a radical of formula (a-1) or a radical of formula (a-2) wherein Z is O or S; $R^1$ is $C_{1-4}$alkyl or halo; and $R^4$ is $C_{1-4}$alkyloxycarbonyl or a 1,2,4-oxodiazol-5-yl of formula (b-2) wherein $R^6$ represents $C_{1-4}$-alkyl.

3. A compound according to claim 1 wherein Het is a radical of formula (a-1); $R^1$ represents methyl, chloro, bromo or iodo; and $R^4$ is methoxycarbonyl, ethoxycarbonyl or 3-ethyl-1,2,4-oxadiazol-5-yl.

4. A compound according to claim 1 wherein Het is a radical of formula (a-2) wherein Z is O or S; $R^1$ represents methyl, chloro, bromo or iodo; and $R^4$ is methoxycarbonyl, ethoxycarbonyl or 3-ethyl-1,2,4-oxadiazol-5-yl.

5. A compound according to claim 1 wherein the compound is ethyl 2-[[-1-(6-chloro-3-pyridazinyl)-4-piperidinyl]methyl]-6-benzothiazolecarboxylate, ethyl 5-[2-[1-(6-methyl-3-pyridazinyl)-4-piperidinyl]ethoxy]-2-thiophenecarboxylate or ethyl 2-[2-[1-(6-chloro-3-pyridazinyl)-4-piperidinyl]ethyl]-5-benzoxazolecarboxylate.

6. A method of inhibiting, combating or preventing the growth of picornaviruses in warm-blooded animals by the systemic or topical administration of an anti-picornavirally effective amount of a compound of formula (I) as claimed in claim 1.

7. A method according to claim 6 wherein Het is a radical of formula (a-1) or a radical of formula (a-2) wherein Z is O or S; $R^1$ i $C_{1-4}$alkyl or halo; and $R^4$ is $C_{1-4}$alkyloxycarbonyl or a 1,2,4-oxadiazol-5-yl of formula (b-2) wherein $R^6$ represents $C_{1-4}$alkyl.

8. A method according to claim 6 wherein Het is a radical of formula (a-1); $R^1$ represents methyl, chloro, bromo or iodo; and $R^4$ is methoxycarbonyl, ethoxycarbonyl or 3-ethyl-1,2,4-oxadiazole-5-yl.

9. A method according to claim 6 wherein Het is a radical of formula (a-2) wherein Z is O or S; $R^1$ represents methyl, chloro, bromo or iodo; and $R^4$ is methoxycarbonyl, ethoxycarbonyl or 3-ethyl-1,2,4-oxadiazol-5-yl.

10. A method according to claim 6 wherein the compound is ethyl 2-[[-1-(6-chloro-3-pyridazinyl)-4-piperidinyl]methyl]-6-benzothiazolecarboxylate, ethyl 5-[2-[1-(6-methyl-3-pyridazinyl)-4-piperidinyl]ethoxy]-2-thiophenecarboxylate or ethyl 2-[2-[1-(6-chloro-3-pyridazinyl)-4-piperidinyl]ethyl]-5-benzoxazolecarboxylate.

11. An anti-picornaviral composition comprising an inert carrier and, if desired, other additives, and as active ingredient an anti-picornavirally effective amount of a compound of formula (I) as claimed in claim 1.

12. A composition according to claim 11 wherein Het is a radical of formula (a-1) or a radical of formula (a-2) wherein Z is O or S; $R^1$ is $C_{1-4}$alkyl or halo; and $R^4$ is $C_{1-4}$alkyloxycarbonyl or a 1,2,4-oxadiazol-5-yl of formula (b-2) wherein $R^6$ represents $C_{1-4}$alkyl.

13. A composition according to claim 11 wherein Het is a radical of formula (a-1); $R^1$ represents methyl, chloro, bromo or iodo; and $R^4$ is methoxycarbonyl, ethoxycarbonyl or 3-ethyl-1,2,4-oxadiazol-5-yl.

14. A composition according to claim 11 wherein Het is a radical of formula (a-2) wherein Z is O or S; $R^1$ represents methyl, chloro, bromo or iodo; and $R^4$ is methoxycarbonyl, ethoxycarbonyl or 3-ethyl-1,2,4-oxadiazol-5-yl.

15. A composition according to claim 11 wherein the compound is ethyl 2-[[1-(6-chloro-3-pyridazinyl)-4-piperidinyl]methyl]-6-benzothiazolecarboxylate, ethyl 5-[2-[1-(6-methyl-3-pyridazinyl)-4-piperidinyl]ethoxy]-2-thiophenecarboxylate or ethyl 2-[2-[1-(6-chloro-3-pyridazinyl)-4-piperidinyl]ethyl]-5-benzoxazolecarboxylate.

16. A composition according to any of claims 1, and 12–15 further comprising a cyclodextrin or a derivative thereof.

* * * * *

UNITED STATES PATENT AND TRADEMARK OFFICE
CERTIFICATE OF CORRECTION

PATENT NO.  : 5,112,825
DATED       : May 12, 1992
INVENTOR(S) : Raymond A. Stokbroekx; Marcel J. M. Van der Aa It is certified that error appears in the above-indentified patent and that said Letters Patent is hereby corrected as shown below:

Column 34, at line 27 and at line 54, delete the hyphen "[-]" that occurs between "ethyl 2-[[" and "1".

Signed and Sealed this

Seventeenth Day of May, 1994

Attest:

BRUCE LEHMAN

*Attesting Officer*   *Commissioner of Patents and Trademarks*